US007087376B2

(12) United States Patent
Miller

(10) Patent No.: US 7,087,376 B2
(45) Date of Patent: Aug. 8, 2006

(54) DETECTION AND IDENTIFICATION OF BACTERIAL STRAINS

(75) Inventor: Stefan Miller, Regensburg (DE)

(73) Assignee: Profos AG (DE)

(*) Notice: Subject to any disclaimer, the term of this patent is extended or adjusted under 35 U.S.C. 154(b) by 0 days.

(21) Appl. No.: 10/060,618

(22) Filed: Jan. 30, 2002

(65) Prior Publication Data
US 2002/0127547 A1 Sep. 12, 2002

Related U.S. Application Data

(63) Continuation of application No. PCT/DE00/02495, filed on Jul. 28, 2000.

(30) Foreign Application Priority Data
Feb. 8, 2001 (DE) ................................ 199 36 047

(51) Int. Cl.
C12Q 1/00 (2006.01)
C12Q 1/02 (2006.01)
C12Q 1/04 (2006.01)
C12Q 1/70 (2006.01)
G01N 33/53 (2006.01)

(52) U.S. Cl. .............................. 435/5; 435/4; 435/7.1; 435/7.2; 435/7.32; 435/29; 435/30

(58) Field of Classification Search ................ 436/518, 436/527, 514, 172; 435/7.2, 7.9, 5, 6, 4, 435/2, 235, 7.32, 7.92, 7.1, 29, 30, 7.8, 7.95, 435/7.93, 235.1; 422/82.02, 82.05; 530/387.3, 530/387.1, 412, 300, 350
See application file for complete search history.

(56) References Cited

U.S. PATENT DOCUMENTS

| | | | | |
|---|---|---|---|---|
| 4,797,363 A | * | 1/1989 | Teodorescu et al. | 435/173.3 |
| 5,168,037 A | * | 12/1992 | Entis et al. | 422/58 |
| 5,236,826 A | * | 8/1993 | Marshall | 422/57 |
| 5,447,836 A | * | 9/1995 | Wolber et al. | 435/170 |
| 5,712,172 A | * | 1/1998 | Huang et al. | 422/56 |
| 5,759,774 A | * | 6/1998 | Hackett et al. | 435/2 |
| 5,824,468 A | | 10/1998 | Scherer et al. | 435/5 |
| 5,919,617 A | * | 7/1999 | Bhattacharjee et al. | 435/6 |
| 5,981,179 A | * | 11/1999 | Lorinez et al. | 435/183 |
| 6,022,748 A | * | 2/2000 | Charych et al. | 436/527 |
| 6,319,668 B1 | * | 11/2001 | Nova et al. | 435/6 |
| 6,355,445 B1 | * | 3/2002 | Cherwonogrodzky et al. | 435/188 |

FOREIGN PATENT DOCUMENTS

| | | |
|---|---|---|
| EP | 0143107 | 6/1985 |
| WO | WO 93/17129 | 9/1993 |
| WO | WO 94/06931 | 3/1994 |
| WO | WO 97/22713 | 6/1997 |
| WO | WO 98/42864 | 10/1998 |
| WO | WO 98/48042 | 10/1998 |

OTHER PUBLICATIONS

Schlehuber et al., "A novel type of Receptor Protein, Based on the Lipocalin Scaffold, with Specificty for Digoxigenin," Jouranl of Mol. Biol., vol. 297, pp. 1105-1120 (2000).*
Jayaraman et al., Biotechnology Progess, vol. 13, pp. 837-843 (1997).*
Baxa et al., Biophysical Journal, vol. 71 No. 4, pp. 2040-2048 (Oct. 1996).*
Suzuki et al., Virus Research, vol. 60 No. 1, pp. 95-99 (Mar. 1999).*
Inagaki et al., Journal of Biochemistry, vol. 127 No. 4, pp. 577-583 (Apr. 2000).*
Bowie et al., Science, vol. 247 No. 4948, pp. 1306-1310 (Mar. 1990).*
Apte et al., "Rapid detection of faecal coliforms in sewage using a colorimetric assay of β-D-Galactosidase," Wat. Res., 29:1803-1806, 1995.
Blasco et al., "Specific assays for bacteria using phage mediated release of adenylate kinase," J. Appl. Microbiol., 84:661-666, 1998.
Lanzetta et al., "An improved assay for nanomole amounts of inorganic phosphate," Anal. Biochem., 100:95-97, 1979.
"Principles in adsorption to polystyrene," Nunc Laboratories Bulletin, No. 6, 1-8.
Bennett et al., "The use of bacteriophage-based systems for the separation and concentration of Salmonella," J. Applied Microbiology, 83:259-265, 1997.
Fleminger et al., "Oriented immobilization of periodate-oxidized monoclonal antibodies on amino and hydrazide derivatives of eupergit C," Applied Biochemistry and Biotechnology, 23:123-137, 1990.
Fuchs et al., "In vitro folding pathway of phage P22 tailspike protein," Biochemistry, 30(26):6598-6604, 1991.
Iwashita and Kanegasaki, "Enzymic and molecular properties of base-plate parts of bacteriophage P22," Eur. J. Biochem., 65:87-94, 1976.
King and Laemmli, "Polypeptides of the tail fibres of bacteriophage T4," J. Mol. Biol., 62:465-477, 1971.
Riede, "Receptor specificity of the short tail fibres (gp12) of T-even type *Escherichia coli* phages," Mol. Gen. Genet., 206:110-115, 1987.

* cited by examiner

Primary Examiner—James C. Housel
Assistant Examiner—Zachariah Lucas
(74) Attorney, Agent, or Firm—Fulbright & Jaworski

(57) ABSTRACT

The present invention relates to a method to detect bacteria, the method comprising the following steps: coupling of the bacteriophages and/or bacteriophage proteins to a support, incubating the support coupled with the bacteriophages and/or bacteriophage proteins with a sample, optionally removing the sample and the bacteria in the sample not bound to the bacteriophages and/or bacteriophage proteins, optionally adding substances permeabilizing or destroying the bacterial membrane, and detecting the bacteria in the sample bound to the bacteriophages and/or bacteriophage proteins, wherein the bound bacteria are not subjected to a cultivation step.

13 Claims, No Drawings

DETECTION AND IDENTIFICATION OF BACTERIAL STRAINS

This application claims priority to and is a continuation of PCT application PCT/DE 00/02495, filed on Jul. 28, 2000, and German application DE 199 36 047.2, filed Feb. 8, 2001. The entire content of both these applications are incorporated by reference.

BACKGROUND OF THE INVENTION

I. Field of the Invention

The present invention relates to a method to detect bacteria, the method comprising the following steps: coupling bacteriophages and/or bacteriophage proteins to a support, incubating the support coupled to the bacteriophages and/or bacteriophage proteins with a sample, optionally removing the sample and the bacteria in the sample not bound to the bacteriophages and/or bacteriophage proteins, optionally adding substances permeabilizing or destroying the bacterial membrane, and detecting the bacteria of the sample bound to the bacteriophages and/or bacteriophage proteins, wherein the bound bacteria are not subjected to any cultivation step.

II. Related Art

The rapid and exact detection of bacteria is the first essential step for the diagnosis and treatment of a bacterial infection in human and animals as well as to initiate preventive measures. Furthermore, the detection is useful to control hygienic and quality of raw materials and processed foodstuff and for the control of hygienic and quality of fresh water and washing water and of water quality of public pools. Additionally, the detection is useful for process monitoring and optimization and for quality control in environmental analytics. Quite in contrast to most of the previously applied procedures, the method described herein also allows a simple detection at the place of need.

The detection of bacteria in biological samples in most cases occurs by means of a combination of cultivating methods by monitoring metabolic activities. For the purpose of phage-typing of bacterial strains of one type of bacteria cultivating methods having a sensitivity for bacteria are coupled to typing bacteriophages. This method involves a dense bacterial lawn on an agar plate of the sample to be analyzed which is overlaid with a suspension of bacteriophages in soft agar, said bacterial lawn having been obtained by isolating a single colony, and subsequent multiplication of said colony. The result is obtained after incubation overnight at the optimum bacterial growth temperature, which usually is 37° C. in most cases, by counting the plaques and by the control of the plaque morphology. A typing variant considers the measurement of adenylate kinase subsequent to phage-mediated cell lysis. In this method, an overnight culture of the bacteria to be analyzed is diluted in buffer, phages are added to it, and lysis is measured by means of specific phages per adenylate kinase activity.

In all methods described thus far, detection does not occur prior to lysis, or detection occurs via lysis. This allows monitoring of sources of infection and detection of sources of infection. This typing has been established for years in regard of numerous bacteria such as *Salmonella typhi, Salmonella paratyphi B, Staphylococcus aureus, Pseudomonas aeruginosa* as well as a number of further bacteria. These established detection methods yield a result only after several days in most cases. However, on the other hand, it is the rapid and exact determination of the type of bacteria (typing) that is of great importance for a rapid reaction.

Recently, more rapid molecular biological detection methods such as the polymerase chain reaction have been employed, which methods have the drawback, however, that they are more prone to contaminations. Likewise, with these methods the result is regularly available only after one day.

Furthermore, identification of the bacterial genus in some cases even requires the submission of samples to highly specialized reference laboratories, likewise resulting in a time and cost intensive factor.

SUMMARY OF THE INVENTION

Accordingly, the invention is based on the object to provide a rapid and economic detection method for bacteria, which method can be carried out by especially microbiologically trained staff in the laboratory on the one hand and on the other hand also in a simplified modification at the place of need and without the corresponding previous knowledge. The object is solved by the subject matter defined in the claims.

One aspect of the present invention is thus a rapid and exact detection system for bacteria providing information on the type of bacteria and the bacterial strain, and optionally allowing a quantification of the bacteria, which detection system is based on the recognition of these bacteria by bacteriophages or bacteriophage proteins.

The conventional detection methods for bacteria based on bacteriophages include time-consuming cultivation steps and the bacteriophage-mediated lysis of the cells. It is true that the method according to the present invention also utilizes the specific recognition of cells by bacteriophages but in contrast to the thus far described methods, subsequent to the step of specific cell recognition and subsequent to the separation of unspecifically bound bacteria a corresponding binding assay is performed, for example measurement of a spectroscopic (e.g., by means of absorption, fluorescence, bio- or chemiluminescence, or circular dichroism) or electric (e.g., by means of measuring the capacity or change of the electric conductivity) signal change. This enables a detection of the bacteria after a few minutes already rather than after hours and days, respectively, as enabled previously. By a targeted coupling, in particular by a covalent fixation of bacteriophages to suitable supporting structures, e.g., to microtiter plates, test stripes, slides, wafer, filter materials, or flow through cell chambers, the procedural step of the binding assay is favored by a reduction of the unspecific background, and enables a broad application for all bacteria. The supporting structures may consist, as an example, of polystyrene, polypropylene, polycarbonate, PMMA, cellulose acetate, nitrocellulose, glass, silicium wafer. Employment of the method according to the present invention furthermore enables the use of lysogenic bacteriophages for the detection of bacteria.

One aspect of the present invention is therefore the provision of a method to detect bacteria, the method comprising the following steps: coupling of bacteriophages and/or bacteriophage proteins to a support, incubating the support coupled to the bacteriophages and/or bacteriophage proteins with a sample, optionally removing the sample and the bacteria of the sample not bound to the bacteriophages and/or bacteriophage proteins, optionally adding substances permeabilizing or destroying the bacterial membrane, and detecting the bacteria in the sample bound to the bacteriophages and/or bacteriophage proteins, wherein the bacteria bound are not subjected to any cultivation step.

Preferred is a method wherein the detection is carried out by means of a colorimetric detection of cellular components and/or products of the phage reproduction, by means of a detection of DNA and/or RNA or by means of an immunoassay. Also preferred is a method wherein the bacteriophages and/or bacteriophage proteins are coupled to the supports by means of adsorption or by means of a chemical bond. An additionally preferred method is a method, wherein the bacteriophages and/or the bacteriophage proteins exhibit modifications. A further preferred method is a method, wherein at least two different bacteriophages and/or bacteriophage proteins recognizing at least two different types and/or genera of bacteria are employed. A further preferred method is a method, wherein the support is, e.g., a microtiter plate, test stripes, slides, wafer, filter material, or a flow-through cell chamber and, e.g., consists of polystyrene, polypropylene, polycarbonate, PMMA, cellulose acetate, nitrocellulose, glass, or silicium wafer. Bacteriophages specific for the bacteria to be detected desirably are employed for the detection. The phages need not to be specific for only one type of bacteria but may be specific for several types of bacteria or for a bacterial genus. Which phages are employed for the detection depends on which bacteria are to be detected. Furthermore, two or more phages may be used in a single detection method to simultaneously detect several types of bacteria or to type a genus of bacteria exactly. The bacteriophages used may be commercially available bacteriophages from stock collections such as DSM or ATCC, or bacteriophages specifically isolated for this purpose. Both lytic and lysogenic bacteriophages may be employed, the lytic phages being preferred. Their morphologic properties do not limit the phages to be selected, myoviridae (T4-like phages), siphoviridae ((-like phages) or podoviridae (T7-, P22-like phages) being preferred, however.

DETAILED DESCRIPTION OF THE INVENTION

Phages bind the corresponding receptors of the bacteria, resulting in a protein-protein or protein-carbohydrate, or protein-lipid interaction. Subsequent to the highly specific recognition of its hosts the phage injects its genetic information (single-stranded or double-stranded DNA or RNA) into the cell and is either present in its lysogenic form or produces, in case of lysis, new phage particles. The bacterial injection of the nucleic acid of the phages causes the binding of the bacteria to the phages, in most cases in an irreversible manner. According to the method of the present invention, after finalization of the recognition step, the detection of the bacteria will follow. This method is basically applicable to all bacteria, for which phages have been described or can be isolated. Preferred bacteria are bacteria that are relevant for food industry, medicine, or environmental analytics, such as lactic acid bacteria, e.g., leuconostoc, pseudomonas, and enterobacteria, e.g., *E. coli,* salmonella. The step of recognition can be carried out at any temperature ranging from 0° C. to 90° C., preferably at a temperature ranging from 4° C. to 45° C., particularly preferred at a temperature ranging from 15° C. to 37° C., more particularly preferred at a temperature ranging from 20° C. to 37° C., even more particularly preferred at room temperature.

Additionally, it is possible, to isolate and use for the detection distinct phage proteins, e.g., phage receptors, phage adhesines, or portions thereof, e.g., p12 of T4 or p9-tailspike of P22, or variants of these proteins rather than complete phages. Preferred are adhesines irreversibly binding to bacteria, or adhesines the bacterial binding pocket of which has been modified by recombinant or chemical techniques in order to accomplish an irreversible binding. An example for recombinantly modified phage proteins are the "active-site mutants" of the P22-tailspike (cf. Baxa et al., Biophys. J. 71, 2040–2048; 1996). Phage proteins as well as bacteriophages may be used for the method of the present invention.

The bacteriophages and/or bacteriophage proteins used according to the present invention may be adopted to the supporting structures in their host specificity and their binding properties, respectively, by a directed or random mutagenesis. Mutagenesis introduces mutations that can be amino acid additions, deletions, substitutions, or chemical modifications. These mutations have the effect to modify the amino acid sequence in the binding region of the phages or phage proteins aiming at an adaptation of specificity and binding affinity to the assay requirements, e.g. to render the binding of the bacteria to the isolated phage proteins irreversible in order to improve the options to wash. In addition, a recombinant or biochemical modification of the phage proteins may be performed in order to accomplish a switch-off of the enzymatic activity optionally present, thereby improving the binding or rendering it irreversible.

For the purpose of the detection according to the present invention the phages or phage proteins are immobilised on suitable supporting structures, e.g., microtiter plates, test stripes, slides, wafers, filter materials, or flow-through cell chambers. The supporting structures may consist of, e.g., polystyrene, polypropylene, polycarbonate, PMMA, cellulose acetate, nitrocellulose, glass, silicium wafer. The immobilization may be accomplished by adsorption or by covalent binding, wherein the covalent binding is preferred. It is relevant that immobilization is a functional one, that is, the phages and phage proteins, respectively, exhibit structures accessible for bacteria although they are bound to the support material.

In order to suppress an unspecific reaction of the bacteria to be investigated with the support material a blocking with bovine serum albumin or Tween 20 or substances that are likewise employed in ELISAs, such as milk powder, may be performed. Furthermore, to increase the efficiency of the adsorption, the support systems may be precoated with suitable proteins (e.g., specific antibodies against phage proteins or unspecific proteins such as BSA) peptides, saccharides, (e.g., mono-, oligo-, or polysaccharides) or detergents (e.g., Tween 20 or octylglucoside). These coatings may occur overnight at a temperature ranging from 4° C. to 20° C. or within a period of 2 h to 4 h at a temperature of 30° C. to 65° C. Subsequently the excess liquid is removed, and the supporting structure dried at about 60–70° C. The basic coating is to guarantee adsorption of functional phages or phage proteins on the one hand and, on the other hand, to prevent an unspecific adsorption of the test bacteria to the supporting structure, thereby increasing the efficiency of the assay. Following the basic coating, the phages or phage proteins are applied by applying an aqueous buffered solution of the phages or phage proteins to the pre-treated supporting structure. After an adsorption at 4–20° C. overnight or at 30–65° C. for a period of 2–4 hrs the coating solution is removed and the supporting structure is dried as described above. In order to increase the coating efficiency, a covalent fixation of the phages or phage proteins with chemical crosslinkers such as glutaric aldehyde may be performed subsequently.

A phage display approach (cf. Gene, 1998, 215, 439–444), wherein peptides are expressed on the phage head protein or on the capsid proteins, which peptides have defined binding properties for particular supporting systems, may be employed with the phages used, e.g., with myoviridae, siphoviridae and podoviridae, in order to improve the functional immobilization.

The immobilization of the phages and phage proteins to the supporting material by means of adsorption may be performed by incubating a phage solution in aqueous buffer, e.g., 100 mM Tris, pH 7.3 or 100 mM sodium phosphate, pH 7.5, over several hours or over night at 5° C. to 45° C., preferably at 15° C. to 37° C., more preferably at 20° C. to 37° C., still more preferably at room temperature.

There is no need to immobilize the phages or phage proteins directly on the support. Rather, they may be bound to polypeptides which in turn are immobilized on the support. These polypeptides may be antibodies, lectins, receptors, or anticalins specific for the phages or phage proteins.

In case of immobilizing the phages and phage proteins by means of covalent coupling, unspecifically bound bacteria may be better removed due to more stringent washing conditions. For the covalent coupling the phages and phage proteins can be coupled to the support materials previously activated by the manufacturer, e.g., by primary amino groups or by carboxyl groups. Examples of such support materials are, e.g., microtiter plates from Nunc, Xenobind, or Costar. Furthermore, the phages and phage proteins may be covalently coupled with, e.g., —$NH_2$ (Russian Chemical Rev., 1964, 33: 92–103), or $COO^-$ via EDC (1-ethyl-3'(3'-dimethylaminopropyl(carbodiimide) (Anal. Biochem. 1990, 185: 131–135) in standard reactions. Additionally, the support materials may be directly activated by means of suitable methods. One alternative, which is preferred due to its applicability to a broad range of support materials is silanization. For example, silanization of polystyrene may be performed by flame pyrolysis. Subsequently, suitable adhesives allowing a coupling via, e.g., primary amino groups or carboxyl groups are applied.

In order to accomplish a directed immobilization, e.g., for T4-phages a coupling via the "head" to the support, swellable polymers having pores of a defined size or, on metallic surfaces mixtures of alkyl thiols having different lengths may be employed.

To bind the bacteria to be analyzed to the immobilised bacteriophages or phage proteins, the sample to be analyzed is contacted and incubated—in an aqueous form—with the phages or phage proteins. Incubation occurs at a temperature ranging from 4° C. to 90° C., preferably at a temperature ranging from 4° C. to 45° C., more preferably at a temperature ranging from 15° C. to 37° C., even more preferred at a temperature ranging from 20° C. to 37° C., in particular at room temperature, for a time period up to 6 hr, preferably up to 4 hr, more preferably 2 hr, in particular 1 hr, more particularly 1 to 20 min. To give an example, the incubation may be 2 to 120 min at 4° C. to 37° C., preferably 20 to 30 min at 25° C. or 37° C., more preferably 35 min at 37° C. By addition of translation inhibitors such as rifampicin, one may extend the time of incubation to increase binding efficiency. Following the specific recognition and the strong binding of the bacteria, unspecifically bound material may be separated by washing with an aqueous buffer, e.g., with PBS or PBS-Tween, preferably at a neutral pH, e.g., with 50 mM sodium phosphate, pH 7.0. Optionally, these detergents, e.g., Tween 20, Triton X-100, or chaotropic agents, e.g., guanidinium hydrochloride or urea, may be added to the buffer used to increase the washing efficiency. This washing step may be repeated several times, regardless of the sample material used.

Following the separation of unspecifically bound materials, the membrane of the bound bacteria can be permeabilized or, if desired (depending on the detection assay used) destroyed by adding detergents (e.g., sodium dodecylsulfate, octylglucoside), chemicals(e.g., polymyxin B), pore-forming polypeptides (e.g., nisin, holin, mellitin), or proteins (e.g., lysozyme). This membrane permeabilization may be carried out during 5 to 10 min at a temperature ranging from about 10° C. to 50° C. Subsequently, the bacteria bound are detected.

If the sample contacted with the immobilized phages or phage proteins, e.g., in a flow-through chamber or on a filter, there is no stringent necessity to remove it after binding the bacteria to the phages or phage proteins prior to carrying out the detection.

The detection of the proteins bound to phages or phage proteins can be performed by using a colorimetric assay, detecting, e.g., NADH (Bergmeyer & Bern; Methoden der enzymatischen Analyse, Bergmeyer, U. VCH, Weinheim 1974), (-galactosidase activity (Apte et al., 1995, Wat. Res. 29, 1803–1806), or inorganic phosphate (Lanzetta et al., 1979, Anal. Biochem., 100, 95–97). These assays allow the detection of at least $10^4$ cells/ml, but by employment of fluorescence dyes sensitivity can be improved to $10^2$ to $10^3$ cells/ml. The colorimetric assays are generally usable to detect the activity of intracellular membrane or periplasmatic enzymes, or of cell components or products of phage reproduction, e.g., phage proteins or phage nucleic acids. The phage nucleic acids may be additionally modified such that an exogenous nucleic acid, e.g., a gene for the horseradish peroxidase, is cloned into a phage genome. After injection of the phage nucleic acid into the bound bacterium, the exogenous gene is expressed. The activity of the gene products can be detected by means of conventional methods. Furthermore, the exogenous nucleic acid may encode any non-bacterial polypeptide which can be detected then.

The colorimetric assays may be identical for all bacteria to be analyzed, but they may also be specific for particular combinations of bacteria/phages. Measurement of the enzymatic activity of cytoplasmatic or periplasmatic enzymes is performed following a membrane permeabilization of the bound bacteria. Preferably, the reactivity of ubiquitous enzymes, such as lactate dehydrogenase or protein disulfide isomerase, is detected. The selection of enzymes may be adapted to the respective bacterial genus tested or to the statement of the problem specific for the genus. For the colorimetric test assays, chemiluminescence-, or bioluminescence, absorption, fluorescence or circular dichroism detection methods are employed, depending on the sensitivity desired.

The detection of the bacteria bound to the phages or phage proteins may also occur by means of detecting DNA and/or RNA. For this purpose, substances may be used that bind to DNA and/or RNA. Binding to the DNA and/or RNA can occur directly on the basis of a membrane diffusion or, in the alternative, on the basis of a membrane permeabilization. Commercially available fluorescence marker such as ethidium bromide, acridine orange, 4',6'-diamidino-2-phenylindole (DAPI) or SYBR green I and the respective detection protocols described in the literature may be used.

Additionally, detection of the bacteria bound to phages or phage proteins can be done by the detection of newly produced DNA and/or RNA. For this purpose, membrane permeable fluorescence-labeled nucleotides can be incorporated into the newly produced phage DNA an/or RNA.

A further detection method is the hybridization with fluorescence-labeled highly conserved oligonucleotides of the 16S-rRNA (Shine-Dalgarno sequence)and the detection of the hybridization signal via fluorescence. Preferred is the detection method by use of phage proteins or phage ghosts ("empty phage capsids", free of nucleotides), since it reduces the background signal of phage DNA or RNA.

Another detection of the bacteria bound to phages or phage proteins is by employment of polypeptides, e.g., antibodies, coupled to a label, e.g., FITC or alkaline phosphatases directed to cell surface structures of the bacteria, or the employment of lectins directed to cell surface structures of the bacteria, wherein signal development of a, e.g., peroxidase-coupled antibody is monitored photometrically. The cell surfaces of the bacteria recognised by the antibodies or lectins may be, as an example, lipopolysaccharides or membrane proteins. The polypeptides may also be phage proteins identical to the immobilized phage proteins or different than the immobilized phage proteins. Additionally, the detection may occur by using complete phages, either identical with or different than the immobilized phages.

The detection method according to the present invention does not need the use of secondary antibodies. In contrast to the conventional ELISA in which the bacteria to be analyzed are coupled to a support system and detection occurs subsequently via primary and secondary antibodies, a pre-enrichment and selection is carried out by using phage particles coupled to support systems. This decreases sensitivity of the ELISA assay from presently $10^4$ to $10^6$ bacilli/ml (Blasco et al., 1998; J. Appl. Microbiol., 84, 661–666) drastically.

As occasion demands, e.g., fluorescence, luminescence, absorption or circular dichroism, conductivity, or capacity changes of the respective samples in the corresponding standard apparatus are detected. To allow an exact determination of the concentration of the bacteria, a calibrating curve with corresponding standard molecules may be established. To achieve an exact determination of the bacterial genus a number of typing systems previously described in the art may be used. In case of need, novel typing systems, that are suitable combinations of different phages, are constructed and used to exactly determine the strain.

The use of the method according to the present invention allows a rapid and sensitive detection of bacteria. Coupling to suitable supporting structures described above enables a rapid and economic determination of numerous bacterial strains, a very exact determination of the bacterial genus and/or a quantification of bacteria in a single assay. Amongst others, the exact determination of the bacterial genus is important in the field of medical diagnostics pertaining to the epidemiological characterization of the pathogens.

The method of the present invention can be used for a rapid, highly sensitive and economic detection of bacteria in any sample, in particular in the in the area of medicine, food industry and analytics, livestock breeding, fresh water or environmental analytics. The simple realization of the method enables both package solutions for the most important combinations of bacteria and system solutions adapted to the desire of clients and thus, a universal utilization of the method of the present invention. The present invention additionally allows a complete automatization of the method according to the present invention. Furthermore, the method is applicable to all bacteria for which suitable phages are available or will be isolated in future times, or for bacteria for which corresponding typing phages or phage proteins may be generated by selection. The method of the invention additionally qualifies for the use in kits to detect bacteria for "anyone" for the domestic use.

A further aspect of the invention relates to a kit to detect bacteria, the kit comprising a support with immobilized phages or phage proteins and the solutions with the assay reagent necessary for the detection of the bound bacteria. The support may be any of the above described supports, to which the phages or phage proteins are immobilised, as described above. The solutions containing the assay reagents likewise correspond with the substances described for the detection of the bacteria in the method of the present invention. Optionally, the kit may additionally comprise washing solutions as well as enzymes or detergents necessary for disintegration of the bacterial membrane.

The following examples explain the invention but are not considered to be limiting. Unless indicated differently, molecular biological standard methods were used, as e.g., described by Sambrock et al., 1989, Molecular Cloning: A Laboratory Manual, 2nd edition, Cold Spring Harbor Laboratory Press, Cold Spring Harbor, N.Y.

1. Isolation and Purification of the Phages

Purification of the *E. coli* phages T4, T7, [Q9]Qβ, and PhiX174 was performed following the cultivation of the phages on the host bacteria corresponding to the data given by DSM on the basis of standard procedures. In order to accomplish a complete separation of bacteria and bacterial residues, the phage suspension was centrifuged with a low value of rpm (5000×g, 30 min.). To concentrate and isolate the phages, a standard preparative ultracentrifugation and a precipitation with polyethylene glycol was done. Successful separation of the bacteria was controlled via a plating experiment, and afterwards the phages were stored cooled (4° C. to 8° C.) or frozen (−20° C., or −80° C.).

2. Isolation and Purification of the Phage Receptor Structures

The phage receptor structures were separated from intact phages by means of standard protein chemical separation methods, or recombinantly produced and purified by means of protein chemical standard separation methods, and stored as were the complete phage particles.

3. Fixation of the Phages by Means of Absorption $10^8$–$10^2$ phages/ml in aqueous buffer (100 mM Tris, pH 7.4, 150 mM NaCl, 0.03% (w/v) gelatin or 50 mM sodium phosphate, pH 7.0) were directly immobilized via absorption on Nunc Maxisorb plates either in the course of several hours at 37° C. or overnight at 20° C. Subsequently, the phages not bound were removed by washing four times with 100 mM Tris, pH 7.3 or 50 mM sodium phosphate, pH 7.5.

After that, a blocking step was performed to suppress unspecific side reactions of the bacteria with the material of the support system. The support system treated with phages was incubated with the blocking solution PBS (4 mM $KH_2PO_4$, 16 mM $Na_2PO_4$, 115 mM NaCl) and the addition of 0.05–1.00% Tween 20, 1% bovine serum albumin either over night in a temperature range of 4° C. or for 2 h at 37° C., the supernatant was removed, and the support system subsequently dried as described previously.

4. Fixation of the Phages by Covalent Binding

Polystyrene plates from Nunc (CovaLink™) and Costar (with $NH_2$ groups) were activated with cyanuric chloride (48 mg in 3 ml acetone, 45 ml 100 mM sodium phosphate, pH 7.0) following the protocol of the manufacturer. 100–200 µl cyanuric chloride were pipetted into the wells of the plates during a period of 2 minutes, and incubated at room temperature for 5 minutes. Subsequently, three times washing occurred with 100 mM sodium phosphate, pH 7.0, and dried at 50° C. for more than 30 minutes. To achieve coupling the phages were incubated in the wells overnight at room temperature in 100 mM sodium carbonate, pH 10.0. Phages not bound were removed by three times washing with 50 mM sodium phosphate, pH 7.0. The plates as completed were dried or covered with aqueous buffer and stored at 4° C. to 20° C. before use.

5. Detection of the Bound Bacteria by Means of β-Galactosidase Activity

The bacterial samples (200 µl sample/well) were incubated at 37° C. for 35 minutes. Following that, unspecifically bound bacteria were separated by three washing steps using either 200 µl 100 mM Tris, pH 7.0 or 200 µl phosphate buffer, pH 7.0. 200 µwashing buffer with $MgCl_2$ and mercapto ethanol as well as 66 µl ONPG (o-nitropenyl-(D-galactopyranoside, 4 mg/ml) were added for the purpose of the dye assay. The assay sample was incubated at 37° C. and the course of the reaction was followed spectrometrically at 405 nm for several (2–5) hours.

I claim:

1. A method for the detection of bacteria comprising:
  a) coupling at least T4 p12 protein to a support, either by coupling the T4 p12 protein via direct binding to a support or via direct binding of the T4 p12 to a polypeptide, which in turn is immobilized to a support, wherein said T4 p12 lacks enzymatic activity;
  b) incubating the support coupled to the T4 p12 with a sample; and
  c) detecting bacteria bound to the T4 p12 protein, wherein bound bacteria are not subjected to a cultivation step.

2. The method of claim 1, further comprising removing unbound sample from the support.

3. The method of claim 1, further comprising adding to the support one or more substances that permeabilize or destroy bacterial membranes.

4. The method according to claim 1, wherein detection is performed by immunologic detection of cell components.

5. The method of according to claim 4, wherein immunologic detection comprises colorimetric detection.

6. The method according to claim 1, wherein the T4 p12 protein is directly contacted with the support.

7. The method according to claim 6, wherein the direct contact is by adsorption or chemical bonding.

8. The method according to claim 1, wherein the T4 p12 protein is bound to said support through a polypeptide immobilized to the support.

9. The method according to claim 8, wherein the polypeptide immobilized to the support is an antibody, lectin, receptor or anticalin.

10. The method according to claim 1, wherein the T4 p12 protein exhibits one or more modifications.

11. The method according to claim 1, wherein at least two distinct bacteriophage proteins, each recognizing distinct types or genera of bacteria, are immobilized to the support.

12. The method according to claim 1, wherein the support is a microtiter plate, a test stripe, a slide, a wafer, a filter material, or a flow-through cell chamber consisting of polystyrene, polypropylene, polycarbonate, PMMA, cellulose acetate, nitrocellulose, glass, or silicium wafer.

13. The method according to claim 1, to detect bacteria in the areas of medicine, food industry and analytics, livestock breeding, fresh water or environmental analytics.

* * * * *

UNITED STATES PATENT AND TRADEMARK OFFICE
CERTIFICATE OF CORRECTION

| | | |
|---|---|---|
| PATENT NO. | : 7,087,376 B2 | Page 1 of 1 |
| APPLICATION NO. | : 10/060618 | |
| DATED | : August 8, 2006 | |
| INVENTOR(S) | : Stefan Miller | |

It is certified that error appears in the above-identified patent and that said Letters Patent is hereby corrected as shown below:

Title page, item [30], line 1, delete "Feb. 8, 2001" and insert --July 30, 1999-- therefor.

Signed and Sealed this

Twenty-ninth Day of September, 2009

David J. Kappos
*Director of the United States Patent and Trademark Office*